(12) United States Patent (10) Patent No.: US 8,491,637 B2
Matthis et al. (45) Date of Patent: Jul. 23, 2013

(54) ROD-SHAPED IMPLANT ELEMENT FOR THE APPLICATION IN SPINE SURGERY OR TRAUMA SURGERY AND STABILIZATION DEVICE WITH SUCH A ROD-SHAPED IMPLANT ELEMENT

(75) Inventors: Wilfried Matthis, Weiswell (DE); Lutz Biedermann, VS-Villingen (DE); Jürgen Harms, Karlsruhe (DE)

(73) Assignee: Biedermann Technologies GmbH & Co., KG, Donaueschingen (DE)

( * ) Notice: Subject to any disclaimer, the term of this patent is extended or adjusted under 35 U.S.C. 154(b) by 1183 days.

(21) Appl. No.: 11/509,544

(22) Filed: Aug. 23, 2006

(65) Prior Publication Data

US 2007/0049937 A1 Mar. 1, 2007

Related U.S. Application Data

(60) Provisional application No. 60/711,082, filed on Aug. 24, 2005.

(30) Foreign Application Priority Data

Aug. 24, 2005 (EP) .................................. 05018425

(51) Int. Cl.
 *A61B 17/70* (2006.01)
(52) U.S. Cl.
 USPC .......................................... 606/254; 606/264
(58) Field of Classification Search
 USPC ............... 606/246, 254–257, 259–261, 263, 606/264, 277, 262, 60, 250–253, 258, 265–276, 606/278, 279; 623/17.11, 17.13, 17.15, 17.16; 403/223, 229; 411/392; 267/286, 291, 166, 267/167, 169, 170, 174
See application file for complete search history.

(56) References Cited

U.S. PATENT DOCUMENTS 575,451 A * 1/1897 Yost .................................. 267/73
2,343,079 A * 2/1944 Pickwell ......................... 464/60
(Continued)

FOREIGN PATENT DOCUMENTS

CA 2069364 12/1992
DE 10348329 B3 2/2005
(Continued)

OTHER PUBLICATIONS

European Search Report for European Application No. 05018425.8-2318 dated Jan. 26, 2006, 6 pp.

(Continued)

*Primary Examiner* — Jerry Cumberledge
(74) *Attorney, Agent, or Firm* — Christie, Parker & Hale, LLP

(57) ABSTRACT

A rod-shaped implant element is provided for connecting at least two bone anchoring elements. Each bone anchoring element includes an anchoring section to be anchored in the bone and a receiver member to be connected to the rod-shaped implant element. The rod-shaped implant element includes, a longitudinal axis, at least one first length of a rigid section that is configured to cooperate with and be received in the receiver member, a second length of a flexible section adjacent to the rigid section, a bore coaxial to the longitudinal axis and extending through the rigid section and the flexible section, and a core accommodated in the bore, the core having two opposite ends. At least one end of the core is freely movable in the bore when said flexible section is extended or compressed in a direction of the longitudinal axis.

33 Claims, 6 Drawing Sheets

U.S. PATENT DOCUMENTS

| | | | | |
|---|---|---|---|---|
| 2,474,690 A * | 6/1949 | Robinson et al. | | 403/229 |
| 2,477,827 A * | 8/1949 | Robinson | | 403/229 |
| 2,546,026 A * | 3/1951 | Coon | | 174/86 |
| 2,583,900 A * | 1/1952 | Spence | | 131/225 |
| 2,586,556 A * | 2/1952 | Mullikin | | 411/339 |
| 3,018,125 A * | 1/1962 | Cain | | 403/196 |
| 4,854,797 A * | 8/1989 | Gourd | | 411/383 |
| 5,061,137 A * | 10/1991 | Gourd | | 411/510 |
| 5,069,569 A * | 12/1991 | Lieser | | 403/57 |
| 5,320,644 A | 6/1994 | Baumgartner | | |
| 5,423,816 A * | 6/1995 | Lin | | 606/247 |
| 5,433,549 A * | 7/1995 | McGaffigan | | 403/229 |
| 5,672,175 A * | 9/1997 | Martin | | 606/86 A |
| 6,102,912 A * | 8/2000 | Cazin et al. | | 606/86 A |
| 6,162,223 A | 12/2000 | Orsak et al. | | |
| 6,290,700 B1 * | 9/2001 | Schmotzer | | 606/263 |
| 6,736,818 B2 * | 5/2004 | Perren et al. | | 606/63 |
| 6,796,984 B2 * | 9/2004 | Soubeiran | | 606/300 |
| 6,964,686 B2 | 11/2005 | Gordon | | |
| 7,604,653 B2 * | 10/2009 | Kitchen | | 606/257 |
| 7,621,912 B2 | 11/2009 | Harms et al. | | |
| 7,621,940 B2 | 11/2009 | Harms et al. | | |
| 7,722,649 B2 | 5/2010 | Biedermann et al. | | |
| 7,815,665 B2 * | 10/2010 | Jahng et al. | | 606/263 |
| 7,905,908 B2 * | 3/2011 | Cragg et al. | | 606/279 |
| 2003/0191470 A1 | 10/2003 | Ritland | | |
| 2003/0220643 A1 | 11/2003 | Ferree | | |
| 2004/0049190 A1 * | 3/2004 | Biedermann et al. | | 606/61 |
| 2004/0106921 A1 * | 6/2004 | Cheung et al. | | 606/61 |
| 2004/0267260 A1 * | 12/2004 | Mack et al. | | 606/61 |
| 2005/0038432 A1 * | 2/2005 | Shaolian et al. | | 606/61 |
| 2005/0056979 A1 | 3/2005 | Studer et al. | | |
| 2005/0065516 A1 * | 3/2005 | Jahng | | 606/61 |
| 2005/0085815 A1 | 4/2005 | Harms et al. | | |
| 2005/0113919 A1 * | 5/2005 | Cragg et al. | | 623/17.11 |
| 2005/0154390 A1 | 7/2005 | Biedermann et al. | | |
| 2005/0171540 A1 * | 8/2005 | Lim et al. | | 606/61 |
| 2005/0182401 A1 * | 8/2005 | Timm et al. | | 606/61 |
| 2005/0203517 A1 | 9/2005 | Jahng et al. | | |
| 2005/0203519 A1 | 9/2005 | Harms et al. | | |
| 2006/0036240 A1 * | 2/2006 | Colleran et al. | | 606/61 |
| 2006/0049560 A1 * | 3/2006 | Chun et al. | | 267/169 |
| 2006/0142758 A1 * | 6/2006 | Petit | | 606/61 |
| 2006/0189983 A1 * | 8/2006 | Fallin et al. | | 606/61 |
| 2006/0229612 A1 * | 10/2006 | Rothman et al. | | 606/61 |
| 2006/0264937 A1 * | 11/2006 | White | | 606/61 |
| 2006/0282080 A1 * | 12/2006 | Albert et al. | | 606/61 |
| 2007/0198088 A1 | 8/2007 | Biedermann et al. | | |

FOREIGN PATENT DOCUMENTS

| | | |
|---|---|---|
| EP | 0669109 B1 | 8/1995 |
| EP | 1574173 A1 | 9/2005 |
| JP | 07-008504 | 1/1995 |
| JP | 2005/118569 | 5/2005 |
| WO | WO 03/047442 A1 | 6/2003 |
| WO | WO 2004/105577 A2 | 12/2004 |
| WO | WO 2005/044117 A2 | 5/2005 |

OTHER PUBLICATIONS

Office action dated May 21, 2009 for U.S. Appl. No. 10/575,699, 9 sheets.

Final Rejection dated Feb. 22, 2010 for U.S. Appl. No. 10/575,699, 5 sheets.

Office action dated May 18, 2010 for U.S. Appl. No. 10/575,699, 9 sheets.

Office action dated Oct. 12, 2007 for U.S. Appl. No. 10/966,921, 6 sheets.

Interview summary dated Oct. 10, 2008 for U.S. Appl. No. 10/966,921, 4 sheets.

* cited by examiner

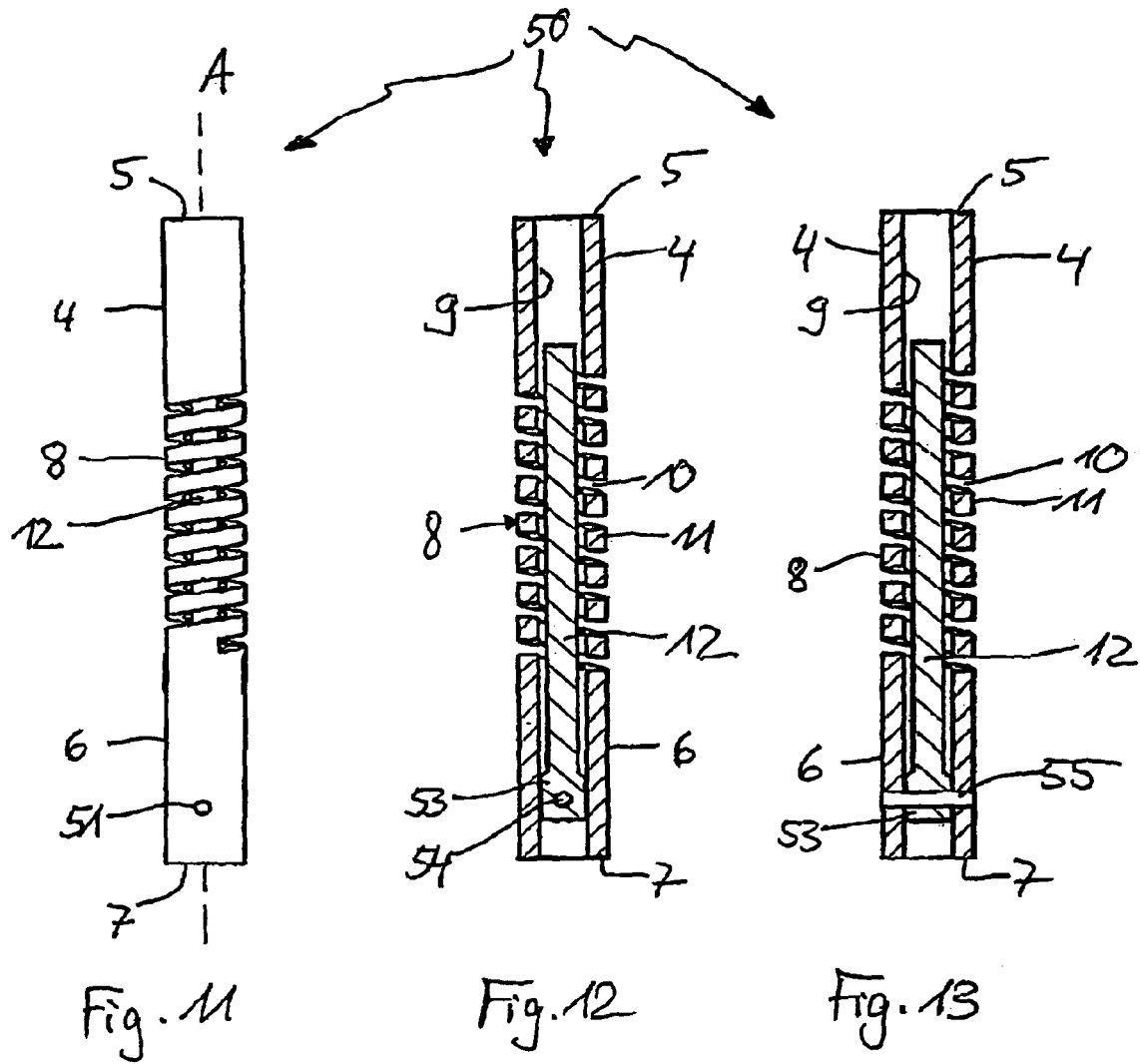

ROD-SHAPED IMPLANT ELEMENT FOR THE APPLICATION IN SPINE SURGERY OR TRAUMA SURGERY AND STABILIZATION DEVICE WITH SUCH A ROD-SHAPED IMPLANT ELEMENT

CROSS-REFERENCE TO RELATED APPLICATION(S)

The present disclosure claims the benefit of U.S. Provisional Patent Application Ser. No. 60/711,082, filed Aug. 24, 2005, and claims priority from European Patent Application EP05018425.8, filed Aug. 24, 2005, the entire disclosures of which are incorporated herein by reference.

BACKGROUND

The present disclosure relates to a rod-shaped implant element for application in spine surgery and/or trauma surgery. The present disclosure further relates to a stabilization device with such a rod-shaped implant element.

Several approaches have been made so far to stabilize the spinal column in the case of intervertebral defects while still allowing a certain degree of motion between the adjacent vertebrae.

EP 0 669 109 B1 discloses a stabilization apparatus for stabilizing neighboring thoracic vertebrae, with which a damaged intervertebral disc and the intervertebral joints can be partly relieved from stress. The apparatus comprises two pedicle screws and a strap that is fixed in the receiver members of each pedicle screw by means of a clamping screw and which further contains a support element that is mounted on the strap and is designed as a pressure-resistant body. However, this stabilization apparatus fails to be torsionally stiff and does not produce any guidance stability of the motion segment of the spinal column.

A joint fixation apparatus, for example for a wrist or a knee joint, is disclosed in U.S. Pat. No. 6,162,223. The apparatus comprises in one embodiment a flexible coupler including an elongated coil spring with two clamps at each end and a flexible cable or a flexible rod extending through the flexible coupler and being fixed at the clamps. Owing to its complex and voluminous structure, this known joint fixation apparatus is not suitable for being used on the spinal column.

US 2003/0220643 A1 discloses a stretchable element to be used in an apparatus for preventing full extension between upper and lower vertebral bodies. The stretchable element may be, for example, an elastic cord or a spring.

US 2003/0191470 A1 discloses an implant device having a rod portion with a center section that flexes when the patient bends their spine. The flexible section can be a linear rod having a variable cross-sectional shape or a non-linear rod having a portion bent in a U-like shape to one side of the axis.

Dynamic stabilization devices are particularly desirable for the treatment of only partially degenerated intervertebral discs. The intervertebral disc should be relieved from stress to support its recovery. If the nucleus of the intervertebral disc is still intact, the intervertebral disc is stiff in the axial direction of the spine (the stiffness is about 500 to 1500 N/mm).

With reference to FIGS. 1 to 5, a known spinal stabilization apparatus for the treatment of degenerated intervertebral discs is shown. Two pedicle screws 2, 3 are anchored in vertebrae 20, 30 which are adjacent to the degenerated intervertebral disc 40 having a nucleus 41, which is still intact. The pedicle screws 2, 3 are connected via a rod-shaped implant element 100 having a helical spring-like section 101 and two rigid sections 102, 103 which serve for the connection with the pedicle screws. FIG. 1 shows the neutral position in which the pedicle screws are spaced apart by a distance x, which changes if the patient bends the spine. In the case of flexion as shown in FIG. 2 or extension as shown in FIG. 3, the nucleus 41 moves in the posterior or anterior direction, respectively, causing the distance between the pedicle screws 2, 3 to decrease or increase relative to the distance x in the neutral position. The decrease and increase of the distance between the pedicle screws 2,3 may vary depending on pathological and anatomical characteristics of an individual. The decrease or increase in the distance between the pedicle screws 2,3 may be nearly the same or different. For example, the decrease and increase can be approximately 1.5 mm and approximately 0.5 mm, respectively, compared to the distance x in the neutral position.

Hence, to allow the flexible section of the rod-shaped implant element to be extended or compressed as required, it has to have a low stiffness or high flexibility in the direction of its longitudinal axis 104. However, if the flexible section 101 has a low stiffness in the axial direction, it also has a low stiffness against bending and shearing forces F as shown in FIG. 5 and bends if such forces occur. This problem arises in the case of use of metal springs as well as in the case of using flexible sections made of other elastic materials such as elastomers.

DE 103 48 329 C1 discloses an elongated rod-shaped implant element comprising a first rigid section to be connected to a bone anchoring element and a second rigid section to be connected to a second bone anchoring element and a flexible section extending between the two rigid sections and formed integrally therewith. The rod-shaped implant element comprises a coaxial bore extending through the element and a core accommodated in the bore, the core being fixed such that it can not slide within the bore.

WO 2004/105577 discloses a spine stabilization system having one or more flexible elements having an opening or a slit in the wall. The flexible element consists of first and second rods which are assembled such that the second rod is fit into a longitudinal bore of the first rod, for example by press-fit.

However, these flexible rod-shaped implant elements do not solve the problem that the rod-shaped implant elements are subject to bending or kinking if they are sufficiently flexible in the axial direction.

In view of the above, there is a need for a rod shaped implant and stabilization device that can remedy one or more of the above described problems associated with current rod shaped implants and stabilization devices.

SUMMARY

In accordance with one or more embodiments of the present disclosure, a rod-shaped implant element and a stabilization device for bones or vertebrae with such a rod-shaped implant element has a stiffness in axial direction so as to allow the bone anchoring elements to move relative to each other in an axial direction but at the same time prevents or reduces bending in a direction which is transverse to the axial direction. The rod-shaped implant element should be easy to manufacture, to adjust and to use.

In accordance with one or more embodiments of the present disclosure, a rod-shaped implant element and the stabilization device allows an axial compression and expansion so as to enable a relative movement of the bone anchoring elements to each other and at the same time prevents bending or kinking. It is particularly suitable for the treatment of partially degenerated vertebral segments.

Further advantages of the disclosure will become apparent from the description of the embodiment in conjunction with the accompanying drawings.

BRIEF DESCRIPTION OF THE DRAWINGS

FIG. 11 shows a side view of a second embodiment of the rod-shaped implant element.

FIG. 12 shows a sectional view of the rod-shaped implant element according to the second embodiment.

FIG. 13 a sectional view rotated by 90" of the rod-shaped implant element of FIG. 12.

DETAILED DESCRIPTION

Figure 1:
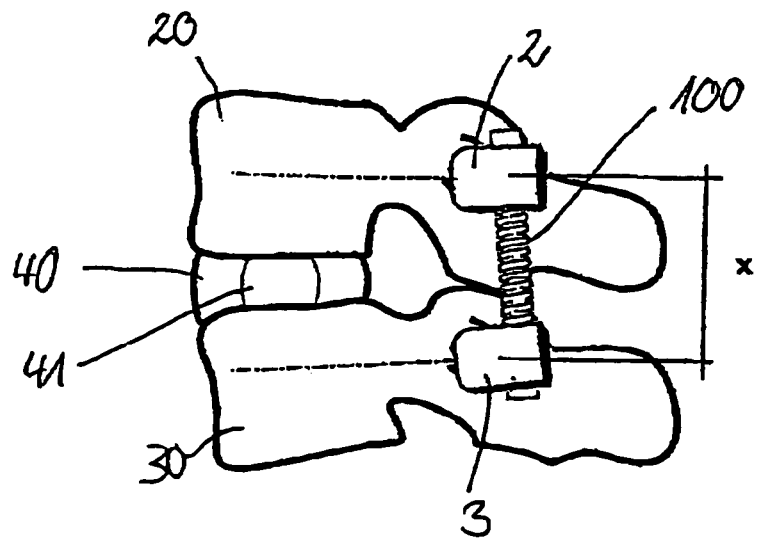
FIG. 1 shows a conventional bone stabilization device in a neutral position of a motion segment of the spine.
Figure 2:
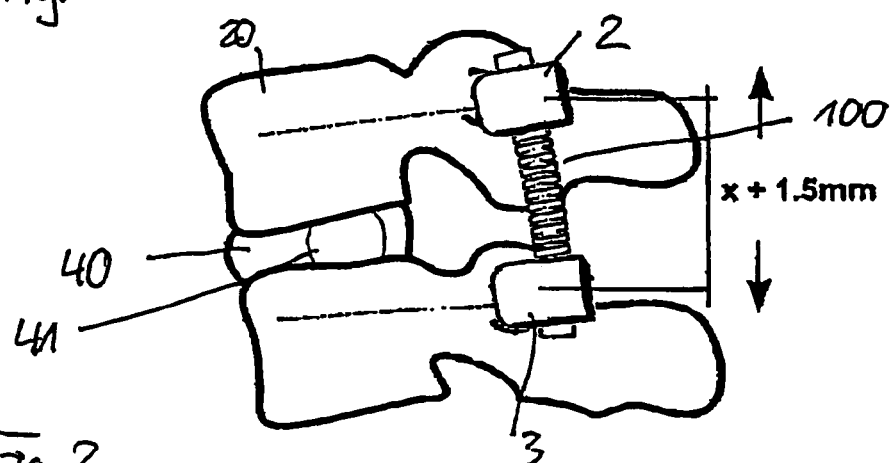
FIG. 2 shows the bone stabilization device of FIG. 1 in a position of flexion.
Figure 3:
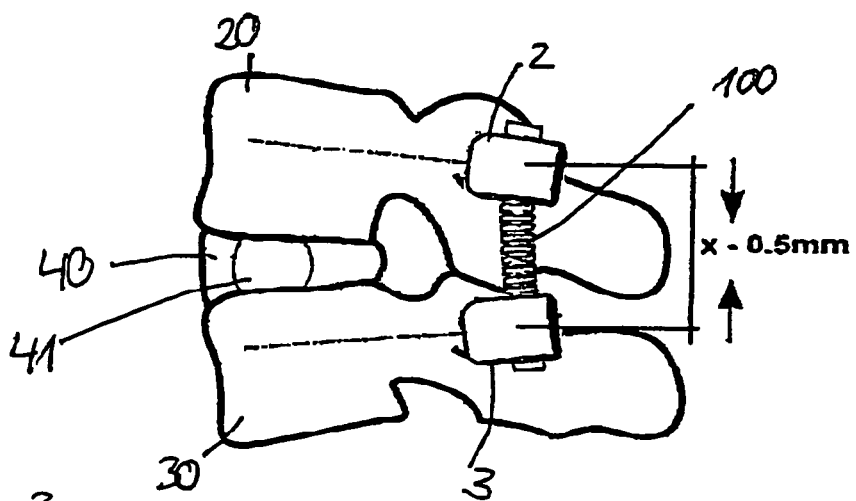
FIG. 3 shows the bone stabilization device of FIG. 1 in a position of extension.
Figure 4:
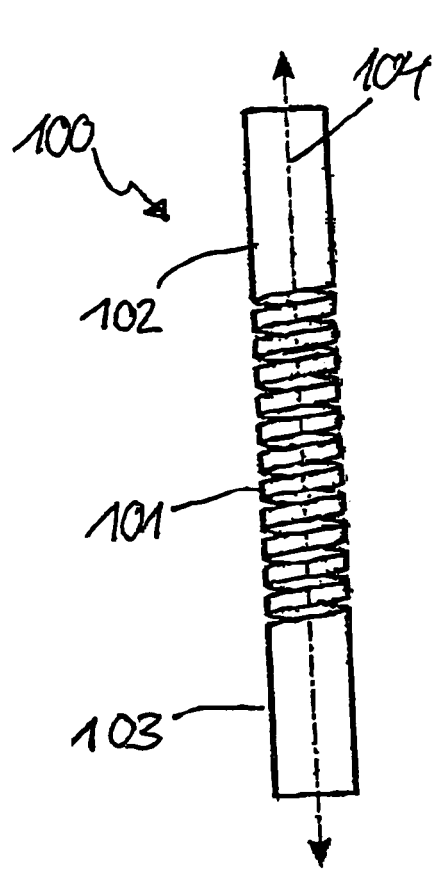
FIG. 4 shows a side view of a known rod-shaped implant element.
Figure 5:
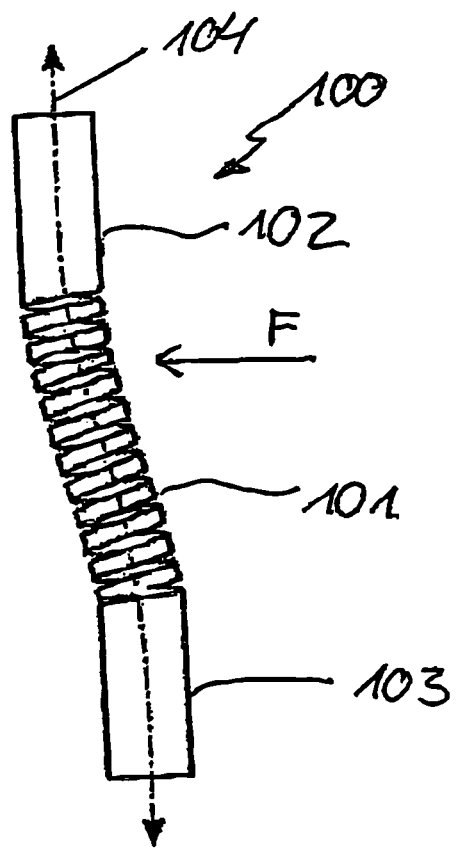
FIG. 5 shows a side view of the known rod-shaped implant element when a bending force acts on the implant element.
Figure 6:
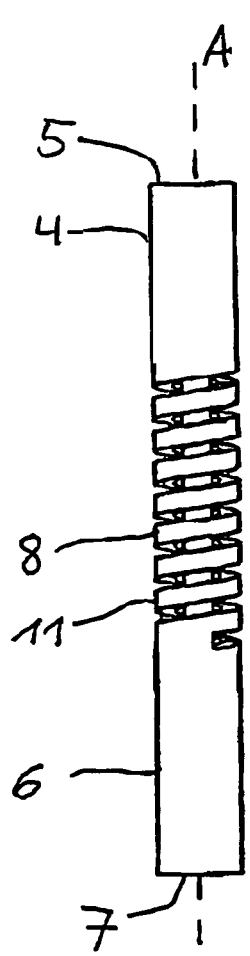
FIG. 6 shows a side view of a first embodiment of the rod-shaped implant element.

As can be seen from FIGS. 6-13 a stabilization device (shown in FIGS. 9 and 10) according to the present disclosure includes a rod-shaped implant element 1 and two pedicle screws 2, 3 which are connected to one another by means of the rod-shaped implant element 1.

The rod-shaped implant element 1 according to the present disclosure includes in the first embodiment a first rigid section 4 that extends across a predefined length from its first end 5 and a second rigid section 6 that extends across a predefined length from its second end 7. The rod-shaped implant also includes a flexible section 8 of a predefined length that is provided between the rigid sections 4, 6. In the embodiment shown, all sections have the same outside diameter. A coaxial bore 9 of a predefined diameter extends through the rod-shaped implant element 1. The flexible section 8 is designed with a helical slotted opening 10 extending radially from the surface to the coaxial bore 9, thereby forming windings 11 of predefined pitch. The helical opening 10 can have straight or tapered sides. The height of the windings 11 of the flexible section 8 in the direction of the longitudinal axis A of the rod-shaped implant element 1, the diameter of the coaxial bore 9 that defines the thickness of the windings 11 in the radial direction, as well as the pitch can be selected such that a desired stiffness towards axial extension and compression forces that are acting on the rod-shaped implant element 1 can be obtained. These dimensions can be varied readily by those skilled in the art to achieve the desired stiffness without undue experimentation.

The rod-shaped element 1 can be made of a biocompatible material, such as titanium, stainless steel or nitinol.

Figure 7:
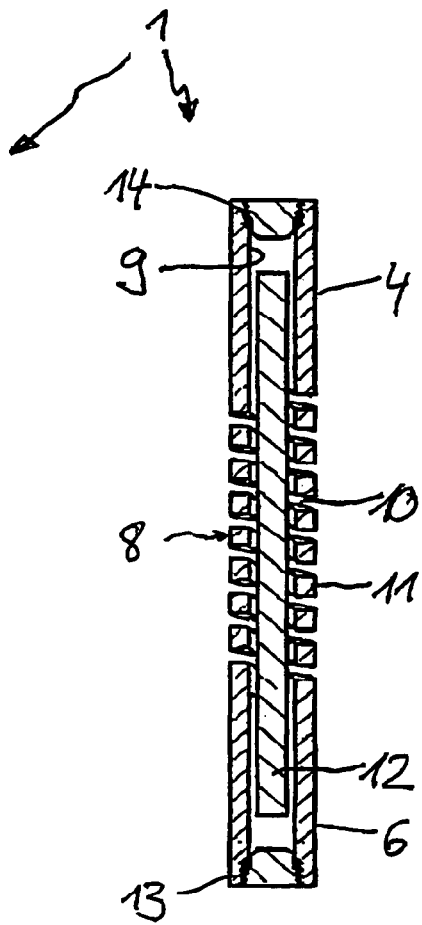
FIG. 7 shows a sectional view of the rod-shaped implant element of FIG. 6 along the longitudinal axis.

As can be seen in particular from FIG. 7, the rod-shaped implant element 1 further includes a core 12, which is of substantially cylindrical shape and has a length which is smaller than the length of the rod-shaped implant element 1, and which has a diameter smaller than the diameter of the coaxial bore 9, such that the core 12 is freely movable and can slide in the axial direction within the bore 9. The length of the core 12 is at least as large as the length of the flexible section 8. In the embodiment shown, the core 12 extends through the flexible section 8 and through a part of the rigid sections 4, 6. The length is selected such that when the flexible section 8 is compressed, the core 12 does not abut to the end of the rigid sections 4, 6. The core 12 is made of a material which has a stiffness against bending forces which is greater than the stiffness of the flexible section 8 of the rod-shaped element 1. Preferably, the core 12 is made of a biocompatible polymer or a metallic substance with a greater stiffness than the flexible section 8. The core 12 is secured within the bore 9 by two closure members 13, 14 provided at each end 5, 7 of the rod-shaped implant element 1. The closure members 13, 14 are shaped to close the bore 9 and are fixed to the rigid sections 4, 6, for example, by a threaded or by a press-fit connection.

Figure 8:
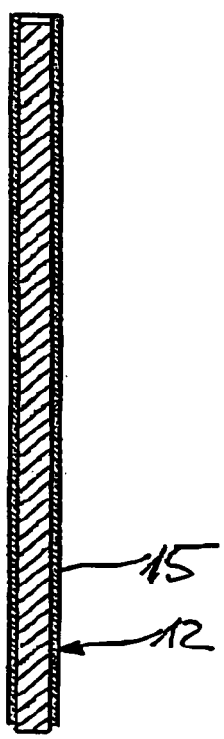
FIG. 8 shows a sectional view of a core of the rod-shaped implant element.

In a preferred embodiment shown in FIG. 8, the core 12 can be coated with a coating 15 made of a material which enables a low-friction sliding of the core 12 with respect to the inner wall of the bore 9. The coating is made for example of polyethylene (PE), Teflon or other materials that reduce friction. For example, a high molecular weight polyethylene of the UHM WPE type with a molecular weight between $2 \times 16^6$ to $10 \times 10^6$ is used as the coating material. The thickness of the coating 15 is selected such that there is no complete abrasion during continuous use of the rod-shaped element 1.

Figure 9:
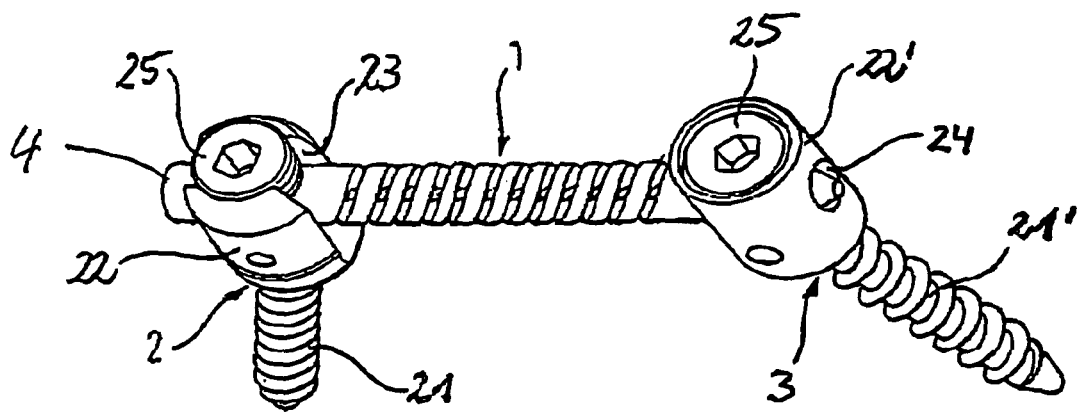
FIG. 9 shows a perspective view of an embodiment of a stabilization device with the rod-shaped implant element according to the disclosure.
Figure 10:
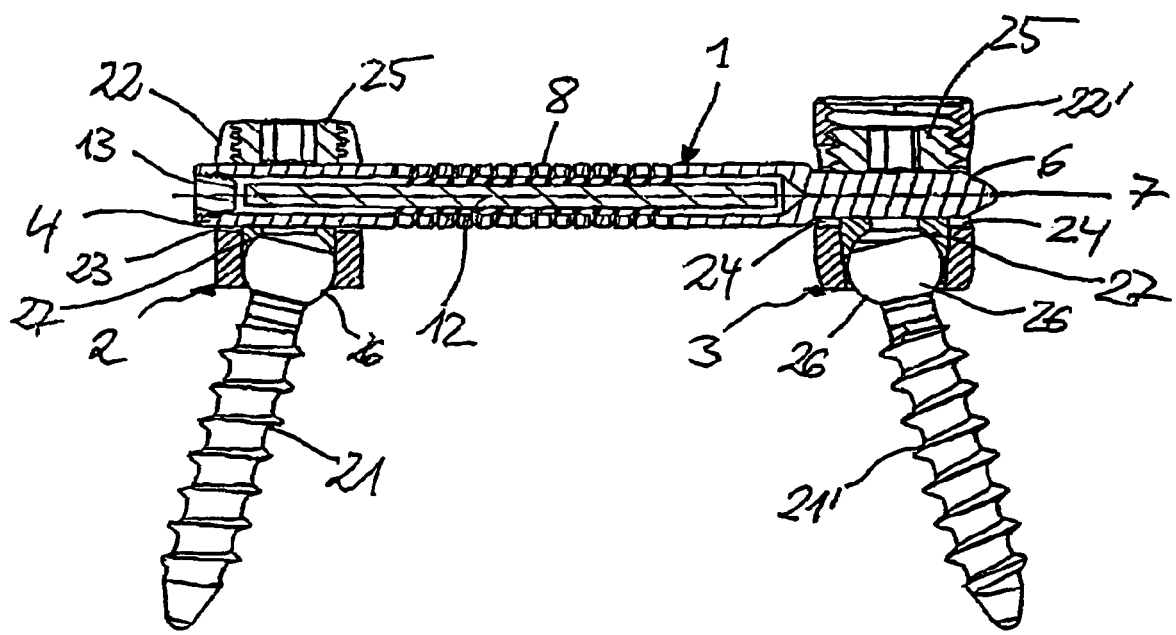
FIG. 10 shows a sectional view of the stabilization device of FIG. 9.

As shown in FIGS. 9 and 10, the length of the flexible section 8 of the rod-shaped implant element 1 is selected such that it essentially corresponds to the distance between the pedicle screws 2, 3 when the pedicle screws are anchored in adjacent vertebrae in a neutral position. Each pedicle screw 2, 3 of the stabilization device comprises an anchoring section 21, 21' having a bone thread for anchoring the pedicle screw 2, 3 in a bone, and an essentially cylindrical receiver member 22, 22' for receiving the rod-shaped implant element 1. In FIGS. 9 and 10, the first pedicle screw 2 comprises a receiver member 22 having a U-shaped recess 23 that opens at the top of the receiver member 22 opposite to the anchoring section 21 for introducing the rigid section 4 of the rod-shaped implant element 1 from the top. The receiver member 22' of the pedicle screw 3 has instead of the U-shaped recess two openings 24 for insertion of the other rigid section 6 of the rod-shaped implant element. The rod-shaped implant element 1 is secured within the receiver members 22, 22' with an inner screw 25 to be screwed into the receiver members 22, 22' from top.

As can be seen in particular from FIG. 10, the pedicle screws 2, 3 are designed as polyaxial screws having a head 26, which is pivotable in the receiver member 22, 22' allowing to adjust the position of the angular position of the receiver member 22, 22' with respect to the anchoring section 21, 21'. The head 26 is locked in its position via a pressure member 27 pressing on the head 26 when the inner screw 25 is tightened.

In the example of the stabilization device shown in FIGS. 9 and 10, the length of the rigid section 4, 6 preferably corresponds approximately to at least the diameter of the fixing element 25 that fixes the rod-shaped implant element 1 in the receiver member 22, 22'. As shown in FIG. 10, the diameter of the second rigid section 6 can be reduced to allow for an easy insertion into the opening 24 of the receiver member 22'. In this case, the coaxial bore 9 does not extend up to the second end 6 so that the second rigid section 7 is still stable enough to be clamped by the inner screw 25 in the receiver member 22'.

In use, first the pedicle screws 2, 3 are anchored in adjacent vertebrae. Then, the rod-shaped implant element 1 is inserted into the receiver members 22, 22' to assume a predetermined position, such as a position corresponding to a neutral position of the flexible section, and fixed by tightening the inner screws 25. Stiffness of the flexible section 8 of the rod-shaped implant element can be selected to provide any desirable extension and compression distance along the axial direction relative to a neutral shape. The extension and the compression distances of the flexible section 8 relative to the neutral shape may be nearly the same or different. However, the extension and compression distances of the flexible section 8 may vary depending on the pathological and anatomical characteristics of an individual. For example, in accordance with one embodiment of the present disclosure, the flexible section 8 of the rod-shaped implant element has a stiffness in the axial direction so as to allow an extension by around 1.5 mm and a compression by around 0.5 mm with respect to a neutral shape. During the flexion and extension of the spinal column, bending forces act on the rod-shaped element, which would cause the flexible section to bend. However, since the core 12 is stiffer than the flexible section 8 of the rod-shaped implant element 1, the core 12 resists bending and the whole rod-shaped implant element 1 does not bend. Therefore, the rod-shaped implant element 1 provides for a guidance stability. It may be necessary for the core 12 to be freely movable with respect to at least one of its ends within the bore 9 to allow extension or compression of the rod-shaped implant element 1.

FIGS. 11 to 13 show a second embodiment of a rod-shaped implant element 50. The rod-shaped implant element 50 of the second embodiment differs from the rod-shaped implant element 1 of the first embodiment in that the core 12 is fixed at one end to the rigid section. Parts which are identical to the first embodiment have the same reference numerals and the description thereof will not be repeated. One of the rigid sections 4, 6 includes a bore 51 extending in a direction transverse to the longitudinal axis A. The bore 51 is located at a certain distance from the second end 7. The core 12 comprises at one end a thickened section 53 the diameter of which is slightly smaller than that of the bore 9 such that the thickened section 53 can still be introduced into the bore 9. A transverse bore 54 is provided in the thickened section 53 at a distance from the free end of the core 12. The core 12 is secured in the bore 9 by means of a pin 55 which is inserted into the bores 51 and 54 when the core 12 is inserted in the rod-shaped implant element 1. In this case, it is not necessary to close the bore 9, since the core 12 cannot slide out of the bore 9. The length of the core 12 is such that it extends at least fully through the flexible section 8. Also in this embodiment, the core 12 can be coated to facilitate sliding within the bore 9. The use of the rod-shaped implant element 1 is the same as in the first embodiment.

Figures 14, 15, 16, 17:
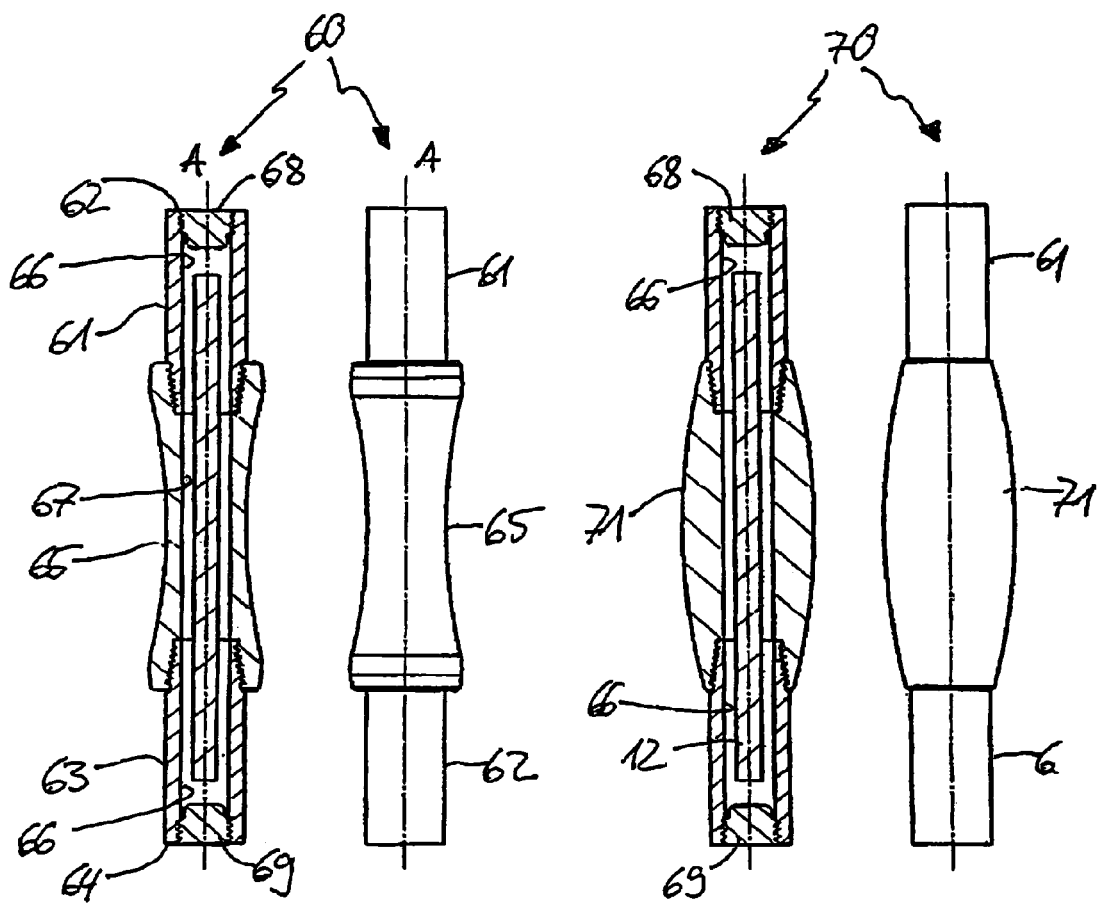
FIG. 14 shows a sectional view of a rod-shaped implant element according to a third embodiment.
FIG. 15 shows a side view of the rod-shaped implant element of FIG. 14.
FIG. 16 shows a sectional view of a rod-shaped implant element according to a fourth embodiment.
FIG. 17 shows a side view of the rod-shaped implant element of FIG. 16.

FIGS. 14 and 15 show a third embodiment of a rod-shaped implant element 60 according to the present disclosure. The rod-shaped implant element 60 of the third embodiment differs from the rod-shaped implant element 1, 50 of the first and second embodiments, respectively, with respect to the design of the flexible section. The rod-shaped implant element 60 has a first rigid portion 61 adjacent to a first end 62, a second rigid portion 63 adjacent to a second end 64 and a flexible section 65 between the first rigid portion 61 and the second rigid portion 63. The first rigid portion 61 and the second rigid portion 63 have a longitudinal coaxial bore 66. The flexible section 65 also has a coaxial bore 67 and is therefore of a substantially tubular shape. At its free ends, the flexible section 65 is connected to the free ends of the first and second rigid portions 61, 63, respectively. The flexible section 65 has an outer diameter which reduces from a first diameter at both ends to a smaller second diameter in the central portion so as to facilitate compression and extension. The rigid sections 61, 63 can be made of a stiff and body compatible material such as, for example titanium, like in the first embodiment. The flexible section 65 can be made of a body compatible elastomer. Such elastomers can be, for example, polyurethanes or polysiloxanes. The flexible section 65 can be fixed to the rigid sections, for example, by means of vulcanization.

As in the first embodiment, a core 12 is provided in the bores 66 and 67 which has such a length so as to freely slide in the bore 9. The free ends 62, 64 of the rigid section 61, 63 are closed by closure members 68, 69 to prevent the core 12 from sliding out of the bore 66, 67.

The use of the rod-shaped implant element 60 of the third embodiment is the same as for the first and second embodiments. Instead of an extension or compression of the helical spring of the first and second embodiments, the elastomer of the flexible portion 65 is extended or compressed.

FIG. 16 and FIG. 17 show a fourth embodiment which is a modification of the third embodiment. The rod-shaped implant element 70 of the fourth embodiment differs from the rod-shaped implant element 60 of the third embodiment according to FIGS. 14 and 15 only in the shape of the flexible section 71. The diameter of the flexible section 71 varies from a first diameter at the ends of the flexible section to a second diameter in the central portion, the second diameter being larger than the first diameter. This rod-shaped implant element 71 is stiffer than the rod-shaped implant of the third embodiment, and is therefore particularly suitable for only small extensions or compressions. The use of is the same as in the previous embodiments.

Modifications are possible. In particular, the elements of the different embodiments can be combined with each other. Combinations of parts of the described embodiments are possible and such combinations are specifically contemplated.

In a modification, the core 12 may be provided with an additional interior strengthening part acting as a core in the core 12. For example, a core made of a biocompatible polymer may be provided with an interior strengthening part made of metal to enhance the core's stiffness. The interior strengthening part may be provided over only part of the length of the core, e.g. its central portion.

The rod-shaped implant element can have several rigid and flexible sections. The diameter of the flexible section can be the same of that of the rigid section or can vary. The core can have several sections with reduced diameter for lowering the stiffness, if required. The core can also be hollow. Further, the core needs not to be cylindrical. It can also have for example a rectangular cross section to provide for an oriented bending stiffness. The core also can have a specific surface treatment such as polishing to lower the friction. If the core is fixed at one end to the rigid section, the fixation can be by any means including for example screwing or gluing. The stabilization device can have other bone anchoring means, for example monoaxial screws or hooks.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A rod-shaped implant element for connecting at least two bone anchoring elements, each bone anchoring element having an anchoring section to be anchored in the bone and a receiver member to be connected to the rod-shaped implant element, the rod-shaped implant element comprising:
a tubular body having a longitudinal axis and comprising:
a first rigid section;
a second rigid section;
a flexible section between the first rigid section and the second rigid section, the flexible section having a predetermined length in a neutral position; and
a bore extending along the longitudinal axis and through the first rigid section, the second rigid section and the flexible section; and
a core accommodated in the bore, the core having two opposite ends, wherein the entire core is freely movable in a direction of the longitudinal axis relative to the tubular body when the flexible section is in an extended condition and a compressed condition in the direction of the longitudinal axis, the extended condition and the compressed condition being relative to the neutral position.

2. The rod-shaped implant element according to claim 1, wherein a bending stiffness of the core is greater than a bending stiffness of the flexible section.

3. The rod-shaped implant element according to claim 1, wherein a surface of the core is coated with a material to facilitate sliding of the core in the bore.

4. The rod-shaped implant element according to claim 3, wherein the material is a plastic material including any one of polyethylene and Teflon.

5. The rod-shaped implant element according to claim 1, wherein the core is made of any one of stainless steel, titanium, nitinol and a stiff plastic material.

6. The rod-shaped implant element according to claim 1, wherein the core comprises a section with a reduced bending stiffness.

7. The rod-shaped implant element according to claim 1, wherein the entire core is located in the bore and is freely movable in the bore in a direction of the longitudinal axis.

8. The rod-shaped implant element according to claim 1, wherein the tubular body is formed as a continuous single part.

9. The rod-shaped implant element according to claim 1, the flexible section comprising an outer surface and a helical slot in the outer surface, the slot extending radially inwards.

10. The rod-shaped implant element according to claim 1, wherein the flexible section is foinied of an elastomer.

11. The rod-shaped implant element according to claim 1, wherein the first rigid section, the second rigid section and the flexible section are secured together independently of the core.

12. An implant comprising:
at least two bone anchoring elements, each bone anchoring element having an anchoring section to be anchored in the bone and a receiver member;
a rod-shaped implant element for connection to the receiver members, the rod-shaped implant comprising:
a tubular body having rigid end sections, a flexible section disposed between the rigid end sections, the flexible section having a predetermined length in a neutral position a bore extending along a longitudinal axis and through the rigid sections and the flexible section; and
a core disposed in the bore;
wherein at least one end of the core is freely moveable in the bore in a direction along the longitudinal axis when the flexible section is in an extended condition and a compressed condition in the direction of the longitudinal axis, the extended condition and the compressed condition being relative to the neutral position.

13. The implant according to claim 12, wherein a bending stiffness of the core is greater than a bending stiffness of the flexible section.

14. The implant according to claim 12, wherein a surface of the core is coated with a material to facilitate sliding of the core in the bore.

15. The implant according to claim 14, wherein the material is a plastic material including any one of polyethylene and Teflon.

16. The implant according to claim 12, wherein the core is made of any one of stainless steel, titanium, nitinol and a stiff plastic material.

17. The implant according to claim 12, wherein the core comprises a section with a reduced bending stiffness.

18. The implant according to claim 12, wherein the entire core is located in the bore and is freely movable in the bore in a direction of the longitudinal axis.

19. The implant according to claim 12, wherein the tubular body is formed as a continuous single part.

20. The implant according to claim 12, the flexible section comprising an outer surface and a helical slot in the outer surface, the slot extending radially inwards.

21. The implant according to claim 12, wherein the flexible section is formed of an elastomer.

22. The implant according to claim 12, wherein the core is slidable in the bore when the flexible section is fully compressed.

23. An implant comprising:
at least two bone anchoring elements, each of which comprise an anchoring section to be anchored in the bone and a receiver member;
a rod-shaped implant element comprising:
a tubular body having a longitudinal axis and comprising:
a first rigid section that is configured to cooperate with and be received in one of the receiver members;
a second rigid section that is configured to cooperate with and be received in the other of the receiver members;
a flexible section between the first rigid section and the second rigid section, the flexible section having a predetermined length in a neutral position; and
a bore extending along the longitudinal axis and through the first rigid section, the second rigid section and the flexible section; and
a core accommodated in the bore, the core having two opposite ends, wherein the entire core is freely movable in a direction of the longitudinal axis relative to the tubular body when the flexible section is in an extended condition and a compressed condition in the direction of the longitudinal axis, the extended condition and the compressed condition being relative to the neutral position.

24. The rod-shaped implant element according to claim 23, wherein a bending stiffness of the core is greater than a bending stiffness of the flexible section.

25. The rod-shaped implant element according to claim 23, wherein a surface of the core is coated with a material to facilitate sliding of the core in the bore.

26. The rod-shaped implant element according to claim 25, wherein the material is a plastic material including any one of polyethylene and Teflon.

27. The rod-shaped implant element according to claim 23, wherein the core is made of any one of stainless steel, titanium, nitinol and a stiff plastic material.

28. The rod-shaped implant element according to claim 23, wherein the core comprises a section with a reduced bending stiffness.

29. The rod-shaped implant element according to claim 23, wherein the entire core located in the bore and is freely movable in the bore in a direction of the longitudinal axis.

30. The rod-shaped implant element according to claim 23, wherein the tubular body is formed as a continuous single part.

31. The rod-shaped implant element according to claim 23, the flexible section comprising an outer surface and a helical slot in the outer surface, the slot extending radially inwards.

32. The rod-shaped implant element according to claim 23, wherein the flexible section is formed of an elastomer.

33. The rod-shaped implant element according to claim 23, wherein the first rigid section, the second rigid section and the flexible section are secured together independently of the core.

* * * * *

UNITED STATES PATENT AND TRADEMARK OFFICE
CERTIFICATE OF CORRECTION

PATENT NO. : 8,491,637 B2  
APPLICATION NO. : 11/509544  
DATED : July 23, 2013  
INVENTOR(S) : Wilfried Matthis et al.

Page 1 of 1

It is certified that error appears in the above-identified patent and that said Letters Patent is hereby corrected as shown below:

On the Title Page

Item (75) Inventors: Delete "Weiswell"  
Insert -- Weisweil --

In the Specification

Column 3, line 32  
After "FIG. 13"  
Insert -- shows --

Delete "90'"  
Insert -- 90°--

In the Claims

Column 7, Claim 10, line 57  
Delete "foinied"  
Insert -- formed --

Column 9, Claim 29, line 17  
After "core"  
Insert -- is --

Signed and Sealed this  
Twenty-fifth Day of February, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,491,637 B2  
APPLICATION NO. : 11/509544  
DATED : July 23, 2013  
INVENTOR(S) : Matthis et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1399 days.

Signed and Sealed this
Twenty-seventh Day of January, 2015

Michelle K. Lee
*Deputy Director of the United States Patent and Trademark Office*